United States Patent [19]

Hughes et al.

[11] Patent Number: 4,743,726

[45] Date of Patent: May 10, 1988

[54] MICROWAVE ACTIVATED HEATING ELEMENT

[76] Inventors: Thomas E. Hughes, P.O. Box 634, Fairhope, Ala. 36533; Calvin L. Seals, 908 Daphine Circle, Daphne, Ala. 36526

[21] Appl. No.: 918,729

[22] Filed: Oct. 14, 1986

[51] Int. Cl.$^4$ ............................................. H05B 6/64
[52] U.S. Cl. .............................. 219/10.55 F; 132/33 R
[58] Field of Search ................. 219/10.55 E, 10.55 F, 219/10.55 R; 132/33 R

[56] References Cited

U.S. PATENT DOCUMENTS 4,390,554 6/1983 Levinson ..................... 219/10.55 E
4,538,630 9/1985 Henderson ............................ 132/33

FOREIGN PATENT DOCUMENTS 3148538 8/1983 Fed. Rep. of Germany .

Primary Examiner—Robert S. Macon
Attorney, Agent, or Firm—Nixon & Vanderhye

[57] ABSTRACT

A microwave activated heating element for exposure to high energy microwaves to heat the element includes a water saturated cellular core, water, heat and flame resistant rubber coated with high temperature lubricant, and a wax center core to absorb and store heat from the microwave heated water and rubber. The construction of the heating element may be accomplished in several forms such as concentrically wound, tubular, layered, and sectioned in particles, to conform to the specific design and use of the outer appliance.

14 Claims, 2 Drawing Sheets

CONCENTRICALLY WOUND

CONCENTRICALLY WOUND

TUBE

LAYER

SECTIONED PARTICLES

EXAMPLE APPLICATIONS

MICROWAVE ACTIVATED HEATING ELEMENT

BACKGROUND OF THE INVENTION

This invention relates generally to appliances requiring radiant heat to perform the function and purpose of their specific design, for example, hair rolling and waving devices, food warmers, heating pads, massagers, and numerous other small household, medical and commercial devices.

Appliances now in use for heating various small household and commercial devices employ electrical heating elements requiring electrical circuits, connecting power cords, batteries, etc. The problem with electrically operated heating appliances is that continuous electric current is needed throughout the period of use. However, the appliances can malfunction, overheat, short-out, and are often left unattended, resulting in the burning out of the appliances or a disastrous fire. A further danger is the possibility of electric shock or electrocution if the appliances are shorted out or immersed in water.

SUMMARY OF THE INVENTION

It is an object of the present invention to provide a radiant heating element that is activated by high frequency microwaves that can be utilized in a variety of devices that employ radiated heat as an agent for primary and secondary application.

It is another object of the present invention to provide a heating element that is activated by high frequency microwaves that comprises a water impregnable cellular core to provide the structure for the suspension of water and other materials and substances composing the heating element. The cellular core and other components of the heating element structure can be tubular; layered, concentrically wound, sectioned in particles, and otherwise sized and shaped to fit various configurations of radiant heat appliances.

It is a further object of the present invention to provide a heating element that is activated by high frequency microwaves, and which can be designed and manufactured in numerous configurations for suitable enclosure in appliances utilizing radiant heat, such as, hair rollers and hair wavers, food warmers, heating pads, massagers, and other small household, medical and commercial devices.

According to the present invention, there is provided a microwave activated heating element comprising an outer structure affording a housing, and accommodating the passage of high frequency microwaves, a flexible cellular core for receiving and suspending water in a cooled or heated state while allowing the passage of high frequency microwaves, said core being dimensioned for reception within the housing and for distribution of the water such that the water may thoroughly saturate and be suspended in the cellular core to receive high frequency microwave energy whereby the rapid buildup of water temperature is effected, a heat and flame resistant flexible rubber element having a predetermined thickness and conformal with the water saturated cellular core, to facilitate reception of high frequency microwave energy.

Each cellular core layer is shaped to fit the required design configuration of the appliance to which the heating element is applied and preferably includes a recess for selectively receiving an application of wax, (which is not ordinarily heatable by high frequency microwaves), having a high melting point. The wax melts when exposed to the transfer of heat from the adjacent components in and around the cellular core, thereby extending the period of heat retention in the heating element, and enhancing the desired measure of heat radiation through and from the appliance. Each cellular core is impregnated with water during the last sequence of assembly of the heating element, facilitating retention of the highest content of moisture in the component prior to sealing of the fully assembled apparatus within the selected appliance.

A flame resistant rubber is provided. The surface of the rubber is coated with a high temperature lubricant to retard flaming, melting, or other deterioration, and to promote heat retention within the rubber.

These materials comprise a heating element, that when activated on a timed basis by the high frequency microwaves, absorb the microwave energy, causing the molecules in the water, rubber, and lubricant to vibrate rapidly, producing a quick heating effect which melts the wax component giving an added heat retention feature. The combination of materials and substance comprising the heating element, when properly insulated and enclosed, retain the heat generated by the rapidly vibrating high frequency microwave activated molecules, sustain the heat and regulate its radiation for a pre-determined period of time dependent upon the length of exposure to the microwave energy, the size of the heating element, and the quantity of component materials, the combination of which provides a rapid heating effect.

These together with other objects and advantages which will become subsequently apparent reside in the details of construction and operation, more fully hereinafter described and claimed, reference being had to the accompanying drawings forming a part hereof, wherein like numerals refer to like parts throughout.

DESCRIPTION OF THE PREFERRED EMBODIMENTS

Figure 1:
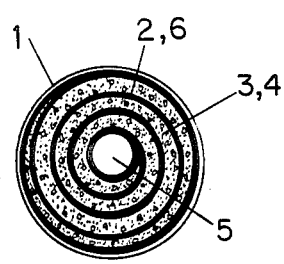
FIG. 1 is a schematic cross-sectional view of a heating element constructed in accordance with the present invention and taken generally about on line 1—1 in FIG. 2.
Figure 2:
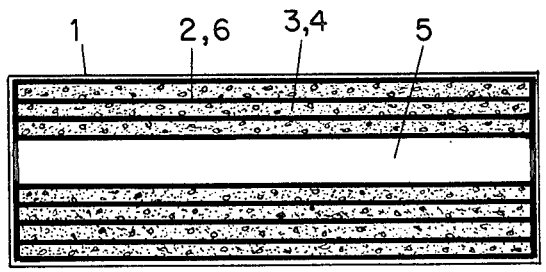
FIG. 2 is a cross-sectional view thereof.
Figure 8:
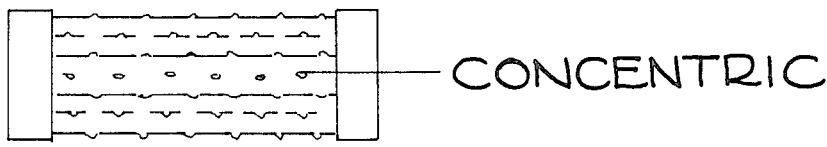
FIGS. 8-12 are various side elevational views of exemplary applications of this invention.
Figure 9:
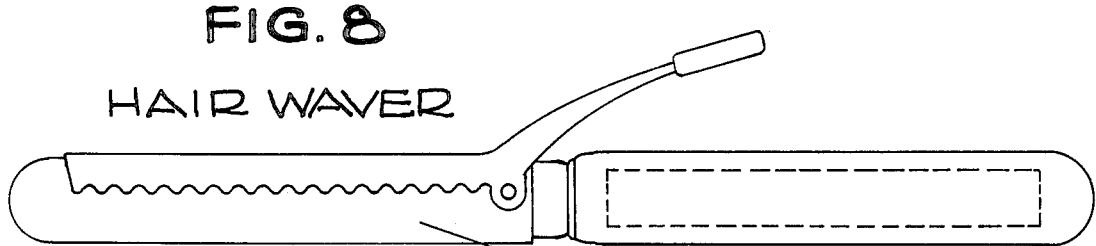
Figure 10:
Figure 11:
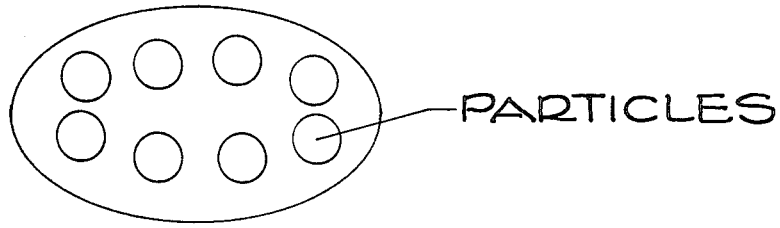
Figure 12:
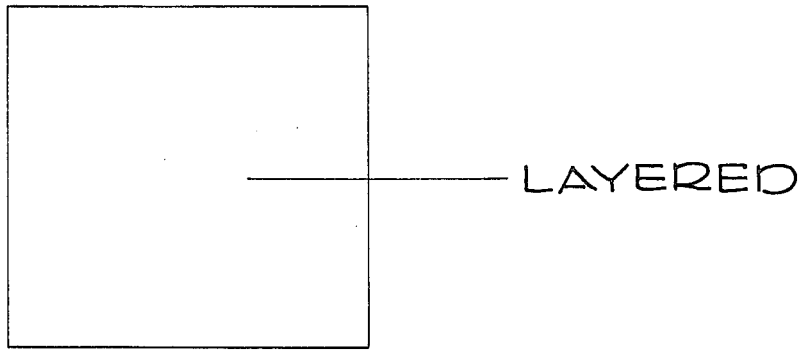

Referring now to FIGS. 1 and 2 of the drawings, a microwave activated heating element constructed according to the present invention, is comprised of a microwavable outer structure (1) compatible to the internal components of the heating element which include a heat and flame resistant rubber (2) coated with a high temperature lubricant (6) assembled together with a water impregnable cellular core (3) saturated with water (4) the whole assembly having at the longitudinal and diametrical center a wax core (5) with a high melting point. Outer structure (1) is provided to contain and protect the internal components of the heating elements (2, 3, 4, 5, 6) and to provide for convenient and easy insertion into appliances, for example as illustrated in FIGS. 8 and 9.

The heating element of FIGS. 1 and 2 is concentrically wound. This is accomplished by placing the wax component (5) in the longitudinal and diametrical center combining together the heat and flame resistant rubber (2) having been coated generously with high temperature lubricant (6) and the sponge-like water impregnated cellular core (3 and 4). Having been properly sized and fitted together, the components (2, 3, 4, 5, and 6) are concentrically wound to form a concentrically wound microwave activated heating element (FIGS. 1 and 2). The heating element (FIGS. 1 and 2) is activated by a timed exposure to a source of high frequency microwaves. As the microwaves pass through the outer structure (1) the molecules in the successive layers of components (2, 3, 4, 6) are activated causing a rapid buildup of heat to occur first in the water molecules contained in the cellular core (3). A slower increase in temperature begins in the heat and flame resistant rubber (2) which continues to build toward a maximum temperature even after the microwave energy is terminated. The high temperature lubricant (6) is generously applied to the surface of the rubber (2) for the purpose of allowing the rubber (2) to be exposed to the microwave energy for a longer period of time, thus allowing the rubber (2) to withstand, contain, and contribute a higher temperature to the heating element as a whole. The wax component (5) does not respond directly to the micro wave energy, however, it absorbs the heat generated from the rubber (2) and water (4) providing a means for a heat retention feature located in the longitudinal and diametrical center of the heating element (FIGS. 1 and 2). The wax (5) melts as it absorbs the microwave generated heat from the rubber (2) and water (4), serving to release the absorbed heat in a slow gradual manner during use, the wax (5) hardening only when it is thoroughly cooled, thus assuring that the maximum possible heat retention is maintained. This novel invention may also be constructed in alternate form with the previously detailed explanation applicable as shown in FIGS. 3–7 for application in appliances such as are shown in FIGS. 8–12.

As can be understood from the above description and from the drawings, a microwave activated heating element according to this invention provides a means for an element with concentrically wound, tubular, and layered components, which when energized by high frequency microwaves, to absorb, generate, and transfer heat which may be used for a variety of applications including hair rollers, hair wavers, food warmers, heating pads, massagers, and other heating appliances in a simple and economical, yet rugged and reliable construction.

Figure 3:
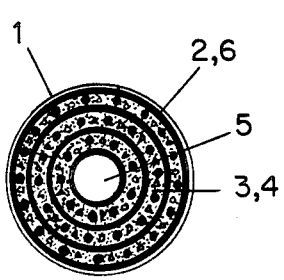
FIG. 3 is a view similar to FIG. 1 illustrating a further embodiment of the present invention and taken generally about on line 3—3 in FIG. 4.
Figure 4:
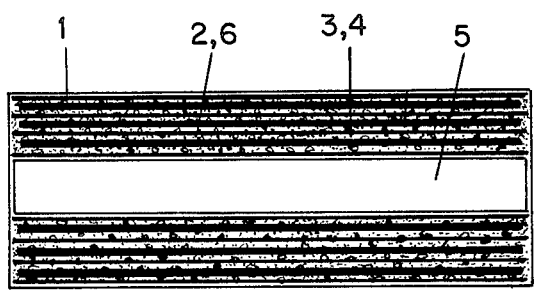
FIG. 4 is a view similar to FIG. 2 illustrating the embodiment hereof of FIG. 3.

While the foregoing heating element has been described in connection with generally spirally arranged materials, the embodiment hereof illustrated in FIGS. 3 and 4 are similar but arranged in concentric layers. In this embodiment, like elements are denoted by like reference numerals followed by the suffix "a". Thus, the concentric rubber tubes or layers 2a are coated with high-temperature lubricant 6a on opposite sides and confine concentrically disposed cellular cores 3a saturated with water 4a. The central core of the heating element is an elongated cylinder of wax 5a. The element of FIGS. 3 and 4 is heated as similarly described with respect to the embodiment hereof illustrated in FIGS. 1 and 2 and similarly used.

Figure 5:
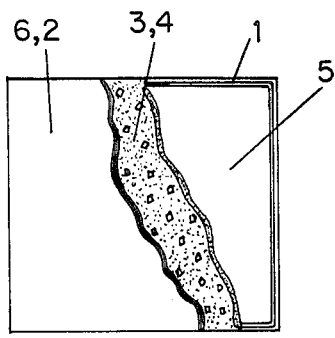
FIG. 5 is a plan view with portions removed illustrating a layered embodiment of this invention.
Figure 6:
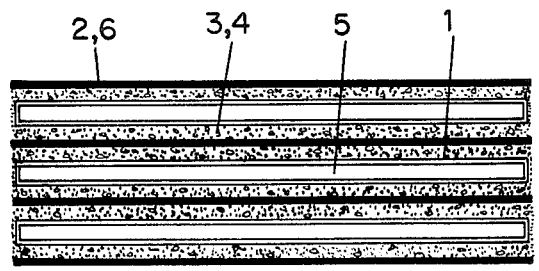
FIG. 6 is a cross-sectional view thereof.
Figure 7:
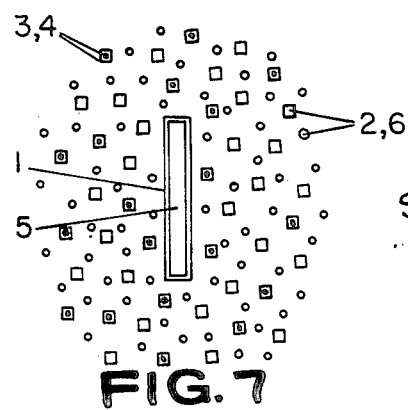
FIG. 7 is an enlarged cross-sectional view showing a sectional and particled embodiment of the present invention.

Referring to FIGS. 5 through 7, like reference numerals are applied to like parts as in the previous embodiments, followed by the suffix "b". In this embodiment, a flat layered heating element is provided having repeating layers of rubber 2b, a lubricant on opposite faces of the rubber, a cellular material 3b impregnable with water 4b and a wax core 5b. The layers may be repeated as desired to form the appropriate thickness.

Referring to FIGS. 8 through 12, there are illustrated various applications of the heating element of the present invention. For example, in FIG. 8, there is illustrated a hair roller for receiving a heating element constructed in accordance with the present invention, for example, either one of the elements of embodiments of FIGS. 1 and 3, respectively. In FIG. 9, there is illustrated a hair curling iron which likewise may receive the cylindrical heating element of the present invention. The layered embodiment of the present invention illustrated in FIGS. 5–7 has application, for example, as a warming dish, illustrated in FIG. 10, as a massager, illustrated in FIG. 11, with the circled portions indicating layered heating elements and as a heating pad, illustrated in FIG. 12.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

Having thus described the invention, what is claimed as new and desired by Letters Patent is:

1. A microwave activated heating element comprising:
    an outer structure affording a housing and accommodating the passage of high frequency microwaves;
    a flexible cellular core for receiving and suspending water in a cooled or heated state while allowing the passage of high frequency microwaves, said core being dimensioned for reception within said housing and for distribution of the water such that the water may thoroughly saturate and lie suspended in the cellular core to receive high frequency microwave energy whereby the rapid buildup of water temperature is effected; and
    a heat and flame resistant flexible rubber element having a predetermined thickness and conformal with the water saturated cellular core to facilitate the reception of high frequency microwave energy.

2. A heating element according to claim 1 wherein said heat and flame resistant rubber is coated at least on one side with a high temperature lubricant to promote heat retention in the rubber.

3. A heating element according to claim 1 including an element within said housing formed of wax for absorbing the heat generated by the water and rubber element to thereby store the heat and release the absorbed heat in a slow, gradual manner.

4. A heating element according to claim 1 wherein said core and said rubber element are spirally wound.

5. A heating element according to claim 1 wherein said core and said rubber element lie in alternate concentric layers within said housing.

6. A heating element according to claim 4 including a core element formed of wax for absorbing heat generated by the water and rubber element, said core element being formed centrally of said housing and within said spirally wound core and rubber element.

7. A heating element according to claim 5 including a core element formed of wax for absorbing heat generated by the water and rubber element, said core element being formed concentrically of said housing and within said concentric layers of said core and rubber element.

8. A heating element according to claim 4 in combination with a hair curler having a central opening, said heating element being disposed in said opening.

9. A heating element according to claim 4 in combination with a hair curler having a central opening, said heating element being disposed in said opening.

10. A heating element according to claim 5 in combination with a hair curler having a central opening, said heating element being disposed in said opening.

11. A heating element according to claim 7 in combination with a hair curler having a central opening, said heating element being disposed in said opening.

12. A heating element according to claim 4 in combination with a hair curling iron, said iron receiving said element.

13. A heating element according to claim 5 in combination with a hair curling iron, said iron receiving said element.

14. A heating element according to claim 1 wherein said rubber element and said core are contained within the housing in alternate layers thereof.

* * * * *